US010821080B2

(12) United States Patent
Raiche et al.

(10) Patent No.: US 10,821,080 B2
(45) Date of Patent: Nov. 3, 2020

(54) MICROENCAPSULATION PROCESS WITH SOLVENT AND SALT

(75) Inventors: Adrian Raiche, Helena, AL (US); Jason Campbell, Helena, AL (US); Heather Nettles, Bessemer, AL (US); Allison Womack, Birmingham, AL (US)

(73) Assignee: Evonik Corporation, Parsippany, NJ (US)

( * ) Notice: Subject to any disclaimer, the term of this patent is extended or adjusted under 35 U.S.C. 154(b) by 0 days.

(21) Appl. No.: 12/562,455

(22) Filed: Sep. 18, 2009

(65) Prior Publication Data

US 2010/0069602 A1 Mar. 18, 2010

Related U.S. Application Data

(60) Provisional application No. 61/097,936, filed on Sep. 18, 2008, provisional application No. 61/146,856, filed on Jan. 23, 2009.

(51) Int. Cl.
*A61K 31/37* (2006.01)
*A61K 31/573* (2006.01)
*A61K 9/16* (2006.01)
*A61K 9/50* (2006.01)

(52) U.S. Cl.
CPC .......... *A61K 9/1694* (2013.01); *A61K 9/1647* (2013.01); *A61K 9/5031* (2013.01); *A61K 9/5089* (2013.01); *A61K 31/37* (2013.01); *A61K 31/573* (2013.01)

(58) Field of Classification Search
USPC ...... 424/93, 497; 428/402–402.24, 407, 403, 428/423.1, 474.4; 427/389.9, 427/213.3–213.36; 264/153, 41, 4–4.7; 257/712, 718; 521/57, 56, 76, 142
See application file for complete search history.

(56) References Cited

U.S. PATENT DOCUMENTS

| 5,407,609 A * | 4/1995 | Tice et al. ............ 264/4.6 |
| 5,945,126 A | 8/1999 | Thanoo et al. |
| 6,777,002 B1 | 8/2004 | Vuaridel et al. |
| 2002/0146456 A1* | 10/2002 | Ramstack et al. ......... 424/489 |
| 2005/0129776 A1* | 6/2005 | Montero-Menei et al. .. 424/489 |
| 2006/0073334 A1* | 4/2006 | Schwantes .......... B01J 13/02 428/402.2 |

(Continued)

FOREIGN PATENT DOCUMENTS

| CA | 2737484 | 9/2009 |
| EP | 09792697.6 | 9/2009 |
| JP | 2011-527985 | 9/2009 |

(Continued)

OTHER PUBLICATIONS

He et al., International J. Pharmaceutics, 309, 101-108 (2006).*

(Continued)

*Primary Examiner* — Jeffrey D Washville
(74) *Attorney, Agent, or Firm* — Linda S. Li; Jason S. Ngui

(57) ABSTRACT

The present disclosure relates to processes for preparing microparticles using an emulsion process where both a solvent and a salt are used in the continuous phase of the emulsion. The present disclosure also relates to microparticles having an angle of repose of ≤35, as measured using a Hele-Shaw cell.

17 Claims, 3 Drawing Sheets

(56) References Cited

U.S. PATENT DOCUMENTS

2006/0110460 A1   5/2006   Ferret et al.

FOREIGN PATENT DOCUMENTS

| JP | 2011-527985 | 11/2011 |
|---|---|---|
| WO | WO-97/41837 A2 | 11/1997 |
| WO | WO-02/051535 A2 | 7/2002 |
| WO | WO 03/092657 A1 | 11/2003 |
| WO | WO 2004/045633 A2 | 6/2004 |
| WO | WO 2004/071634 A2 | 8/2004 |
| WO | 2005087362 A1 | 9/2005 |
| WO | WO 2005/122734 A2 | 12/2005 |

OTHER PUBLICATIONS

He, et al "Stabilization and encapsulation of a staphylokinase variant(K35R) into poly(lactic-co-glycolic acid) microspheres," International Journal of Pharmaceutics, Elsevier BV, NL, XP025113387 309(1-2):101-108 (2006).

Pistel, et al., "Effects of salt addition on the microencapsulation of proteins using W/O/W double emulsion technique," Journal of Microencapsulation, 17(4):467-483 (2000).

International Search Report and Written Opinion issued by International Searching Authority of WIPO on Jan. 13, 2010 for Intl. App. No. PCT/US2009/057437, filed on Sep. 18, 2009 (Inventor—Raiche et al.; Applicant—Surmodics Pharmaceuticals, Inc.; pp. 1-13).

International Preliminary Report on Patentabillity issued by International Bureau of WIPO on Mar. 31, 2011 for Intl. App. No. PCT/US2009/057437, filed on Sep. 18, 2009 (Inventor—Raiche et al.; Applicant—Surmodics Pharmaceuticals, Inc.; pp. 1-8).

Jiao, J. et al. "Rheology and Stability of Water-in-Oil-in-Water Multiple Emulsions Containing Span 83 and Tween 80," MPS PharmSci, 2003, 5(1): 1-12, Article 7.

Reis, C.P. et al., "Nanoencapsulation I. Methods for preparation of drug-loaded polymeric nanoparticles," Nanomedicine: Nanotechnology, Biology, and Medicine, 2006, 2: 8-21.

Response to Communication pursuant to Rules 161(1) and 162 filed on Nov. 17, 2011 for EP Pat. App. No. EP09792697.6, which is national phase of Intl. App. No. PCT/US2009/057437, filed on Sep. 18, 2009 (Inventor—Raiche et al.; Applicant—Surmodics Pharmaceuticals, Inc.; pp. 1-11).

Material Safety Data Sheet, Methylene chloride MSDS. Sciencelab.com, Inc. Nov. 1, 2010, 5 pages.

Matsukura, Yukinori et al., "Angle of Repose: A Matter of Semantics and a Variety of the Measuring Methods," University of Tsukuba, Hydrology Testing Center Reports, No. 13, pp. 27-35 (1989). (translation).

Kwon, Hye-Young et al., "Preparation of PLGA nanoparticles containing estrogen by emulsification-diffusion method," Colloids and Surfaces A: Physicochemical and Engineering Aspects, vol. 182, Issue 1-3, Jun. 30, 2001, pp. 123-130.

* cited by examiner 00261-064-SEM. 250X 0261-063-SEM. 250X 00261-069-SEM. 250X 00261-068-SEM. 250X

MICROENCAPSULATION PROCESS WITH SOLVENT AND SALT

PRIORITY CLAIM

This application claims the benefit of U.S. Provisional Application No. 61/097,936, filed Sep. 18, 2008, and U.S. Provisional Application No. 61/146,856, filed Jan. 23, 2009, each of which is incorporated herein by this reference in its entirety.

FIELD

The present invention relates to processes for preparing microparticles using solvent and salt in the continuous phase.

BACKGROUND

Microparticles have been used to deliver a wide range of active ingredients from perfumes to pharmaceuticals. However, typically in an encapsulation process, an organic solvent is used to dissolve a polymer in the dispersed phase. The polymer is the wall-forming or matrix material of the microparticle. For advantageous processing, the same or similar organic solvent is also used in a saturating solubility quantity in the aqueous based continuous process medium (also referred to the continuous phase). Unfortunately, this leads to processing challenges related, in part, to the large volume of organic solvent in the continuous phase system. Reduction of the amount of organic solvent in the continuous phase system while maintaining the advantageous processing conditions are desired but have not been overcome in the art.

There is therefore a need for a process that can overcome the above deficiencies.

SUMMARY

In accordance with the purposes of the disclosed materials, compositions, articles, devices, and methods, as embodied and broadly described herein, the disclosed subject matter, in one aspect, relates to an encapsulation method for producing microparticles comprising (a) forming an emulsion or double emulsion comprising a dispersed phase comprising an agent, a polymer, and a first solvent for the polymer, in a continuous process medium, wherein the continuous process medium comprises at least one salt and at least one second solvent, wherein the second solvent reduces the solubility of the first solvent in the continuous process medium; and (b) extracting the first solvent from the dispersed phase to form the microparticles.

In another aspect, the disclosed subject matter relates to microparticles made by any process of the inventive disclosed subject matter.

In another aspect, the disclosed subject matter relates to microparticles having an angle of repose of ≤35, as measuring using a Hele-Shaw cell.

In another aspect, the disclosed subject matter relates to an emulsion comprising a dispersed phase comprising an agent, a polymer, and a first solvent for the polymer and a continuous phase comprising a polymer non-solvent, a second solvent, wherein the second solvent reduces the solubility of the first solvent in the polymer non-solvent, and a salt that reduces the solubility of the first solvent in the polymer non-solvent.

Additional advantages will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawing, which is incorporated in and constitutes a part of this specification, illustrates several aspects described below. Like numbers represent the same elements throughout the figures.

DETAILED DESCRIPTION

Figure 1:
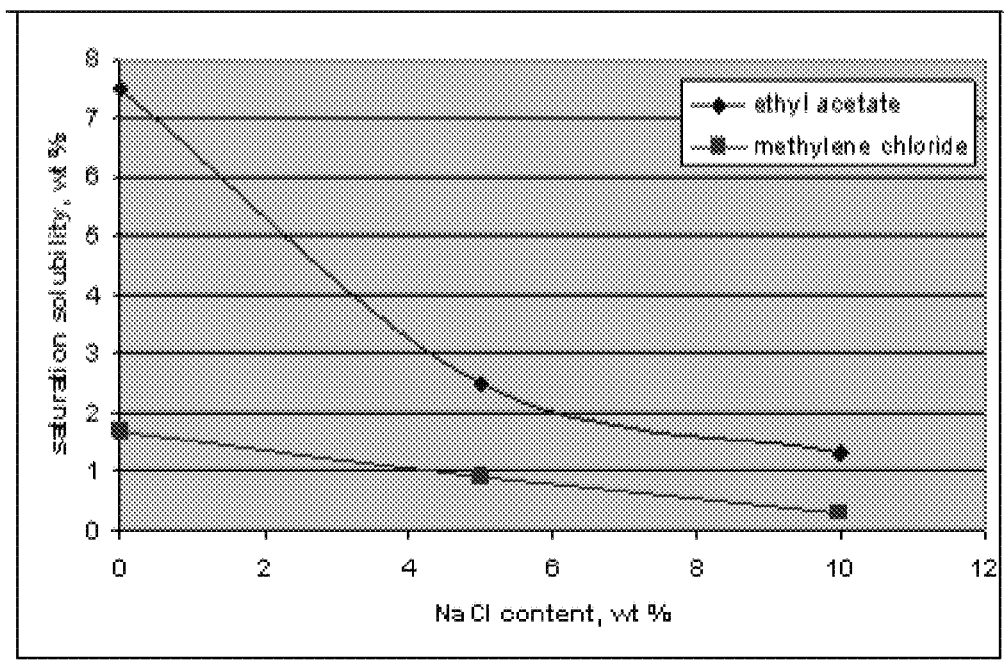
FIG. 1 is a graph showing the saturation solubility in weight percent for the organic solvents ethyl acetate and methylene chloride versus sodium chloride content in weight percent in a 2% PVA aqueous continuous phase solution.

Before the present processes are disclosed and described, it is to be understood that the aspects described herein are not limited to specific processes, compounds, synthetic methods, articles, devices, or uses as such can, of course, vary. It is also to be understood that the terminology used herein is for the purpose of describing particular aspects only and, unless specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

It must be noted that, as used in the specification and the appended claims, the singular forms "a," "an" and "the" include plural referents unless the context clearly dictates otherwise. Thus, for example, reference to "solvent" includes mixtures of two or more such solvents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

"Polymer excipient" or "polymer" as used herein refers to homopolymer or copolymer or blends comprising homopolymers or copolymers and combination thereof that are used as the microparticle wall forming or matrix materials. This term should be distinguished from the term "excipient" as defined herein below.

"Excipient" is used herein to include any other compound or additive that can be contained in or on the microparticle that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients. This term should be distinguished from the term "polymer excipients" as defined above.

"Agent" is used herein to refer generally to a compound that is contained in or on a microparticle composition. Agent can include a bioactive agent or an excipient. "Agent" includes a single such compound and is also intended to include a plurality of such compounds.

The term "microparticle" is used herein to include nanoparticles, microparticles, microspheres, nanospheres, microcapsules, nanocapsules, and particles, in general. As such, the term microparticle refers to particles having a variety of internal structure and organizations including homogeneous matrices such as microspheres (and nanospheres) or heterogeneous core-shell matrices (such as microcapsules and nanocapsules), porous particles, multi-layer particles, among others. In one aspect, the agent is encapsulated in the microparticle. The term "microparticle" refers generally to particles that have sizes in the range of about 10 nanometers (nm) to about 2 mm (millimeters).

The dispersed phase comprises an agent, a polymer, and a first solvent for the polymer. The agent can be any agent that can be encapsulated. Such agents include, but are not limited to, any type of drug or bioactive agent or immunological agent, including small molecules, peptides, proteins, antibodies, nucleic acids, etc.

The polymer can be any polymer used in the encapsulation art. Typically, the polymer is a biocompatible or biodegradable polymer if the microparticle is to be delivered to a living entity. The polymers can be homopolymers or copolymers, including block or blocky co- or ter-polymers, random co- or ter-polymers, star polymers, or dendrimers. Any desired molecular weight polymer can be used, depending on the desired properties of the microparticle. In certain aspects, if a high strength polymer is desired, then high molecular weight polymers can be used, for example, to meet strength requirements. In other aspects, low or medium molecular weight polymers can be used when, for example, when resorption time of the polymer, rather than microparticle strength is desired.

The molecular weight of a polymer can be important given that molecular weight influences the biodegradation rate of a biodegradable polymer. For a diffusional mechanism of bioactive agent release, the polymer should remain intact until all of the drug is released from the polymer and then degrade. The drug can also be released from the polymer as the polymer bioerodes. By an appropriate selection of polymeric materials, a polymer formulation can be made such that the resulting polymer exhibits both diffusional release and biodegradation release properties. Molecular weights can be measured by methods known in the art, including gel permeation chromatography, viscosity, light-scattering, among other methods.

The polymer can be formulated so as to degrade within a desired time interval, once present in a subject, or a biological medium. In some aspects, the time interval can be from about less than one day to about 1 month. Longer time intervals can extend to 6 months, including for example, polymers that degrade from about ≥0 to about 6 months, or from about 1 to about 6 months. In other aspects, the polymer can degrade in longer time intervals, up to 2 years or longer, including, for example, from about ≥0 to about 2 years, or from about 1 month to about 2 years.

The desired bioactive agent release mechanism can influence the selection of the polymer. A biocompatible polymer, for example, can be selected so as to release or allow the release of a bioactive agent therefrom at a desired lapsed time after the implant device has been implanted in a subject. For example, the polymer can be selected to release or allow the release of the bioactive agent prior to the bioactive agent beginning to diminish its activity, as the bioactive agent begins to diminish in activity, when the bioactive agent is partially diminished in activity, for example at least 25%, at least 50% or at least 75% diminished, when the bioactive agent is substantially diminished in activity, or when the bioactive agent is completely gone or no longer has activity.

Examples of suitable polymers include one or more of a poly(lactide), a poly(glycolide), a poly(lactide-co-glycolide), a poly(caprolactone), a poly(orthoester), a poly (phosphazene), a poly(hydroxybutyrate) or a copolymer containing a poly(hydroxybutarate), a poly(lactide-co-caprolactone), a polycarbonate, a polyesteramide, a polyanhydride, a poly(dioxanone), a poly(alkylene alkylate), a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly(oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations, or blends thereof.

Lactide-based polymers can comprise any lactide residue, including all racemic and stereospecific forms of lactide, including, but not limited to, L-lactide, D-lactide, and D,L-lactide, or a mixture thereof. Useful polymers comprising lactide include, but are not limited to poly(L-lactide), poly (D-lactide), and poly(DL-lactide); and poly(lactide-co-glycolide), including poly(L-lactide-co-glycolide), poly(D-lactide-co-glycolide), and poly(DL-lactide-co-glycolide); or copolymers, terpolymers, combinations, or blends thereof. Lactide/glycolide polymers can be conveniently made by melt polymerization through ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

In a particular aspect, when the biodegradable polymer is poly(lactide-co-glycolide), or a mixture of poly(lactide) and poly(glycolide), the amount of lactide and glycolide in the polymer can vary. In a further aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In a further aspect, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide), where the ratios are mole ratios.

In another aspect, the polymer can be a poly(caprolactone) or a poly(lactide-co-caprolactone). In one aspect, the polymer can be a poly(lactide-caprolactone), which, in various aspects, can be 95:5 poly(lactide-co-caprolactone), 85:15 poly(lactide-co-caprolactone), 75:25 poly(lactide-co-caprolactone), 65:35 poly(lactide-co-caprolactone), or 50:50 poly(lactide-co-caprolactone), where the ratios are mole ratios.

The first solvent for the polymer can be any solvent used in dispersed phase that solubilizes or at least partially solubilizes the polymer. The first solvent can be a single solvent or two or more co-solvents. In certain aspects, the first solvent comprises ethyl acetate or methylene chloride.

The continuous process medium typically includes a non-solvent for the polymer, at least one salt and at least one second solvent. The non-solvent for the polymer can be any base solvent for the continuous process medium that is not a solvent for the polymer so that the polymer forms an emulsion when mixed with the continuous process medium. Typical examples of the non-solvent for the polymer include, but are not limited to, an aqueous mixture or solution, or water. In one aspect the continuous process medium further comprises water. In another aspect, the continuous process medium further comprises substantially water.

In one aspect, the salts are one or more ionic salts, metal halide salts (metal halides), salts of alkali metals and halogens, or salts of alkaline earth metals and halogens. The halogens can be F, Cl, Br, or I. In a specific aspect the salt is sodium chloride or potassium chloride.

The salt is typically present at from 0.1 to 20 weight %, 2-20 weight %, or 2-15 weight %, in the continuous process medium. In another aspect the salt is sodium chloride, and is in an amount of from 0.6 to 20 weight % or from 0.1 molar (M) to 3.4 M.

The second solvent is typically one or more organic solvents added to the continuous process medium. The second solvent reduces the solubility of the first solvent for the polymer in the continuous process medium. Saturating the aqueous medium with organic solvent prevents partial emulsion droplet extraction during homogenization. This second solvent can be the same or different from the organic solvent used to prepare the dispersed phase, that is, the second solvent can be the same as or different from the first solvent. In one aspect, the second solvent is the same as any of the first solvents used for the dispersed phase. In certain aspects the second solvent is methylene chloride or ethyl acetate.

The second solvent is typically added to the continuous process medium at levels up to the saturation solubility of the second solvent in the continuous process medium. The actual saturation solubility concentration of the second solvent in the continuous process medium will vary depending upon, among other factors, the amount of salt in the continuous process medium. Typically, the amount of second solvent used is from 0.01 weight % of the continuous process medium up to the saturation solubility of the second solvent in the continuous process medium. In another aspect, the second solvent is added in a range of about 0.1% to 100% of the saturation solubility concentration of the second solvent in the continuous process medium.

In one aspect the second solvent is in a saturating or near saturating amount in the continuous process medium. In one aspect the first and second solvents are the same solvent. In one aspect the first and second solvents comprise organic solvents. In one aspect the second solvent comprises two or more solvents. In another aspect the temperature of the continuous process medium is adjusted to modify (increase or decrease) the solubility of the first solvent in the continuous process medium. In this manner, temperature may also be used, in addition to salt concentration, as an additional means of adjusting the final saturation solubility limit of the first solvent in the continuous phase medium. By changing temperature, the required amount of salt and first solvent in the continuous phase may change, and the ratio of required salt to first solvent may also change to achieve the desired result. Changing amounts of salt or first solvent required or the ratio of the two will affect solvent extraction, volume of extraction, separation and collection among other things.

In one aspect, a surfactant or emulsification agent is used in the continuous process medium. Any surfactant or emulsification agent typically used in encapsulation processes can be used herein. In one aspect the surfactant is polyvinylalcohol (PVA). In these aspects, the PVA can be used from 0.01 weight % to 10 weight %, 0.1 weight % to 5 weight %, or 0.1 weight % to 2 weight % of the continuous process medium. Typically, the concentration of the surfactant or emulsification agent is adjusted as needed in order to remain soluble at a given composition of salt and second solvent concentration level. At certain concentrations of the salt, second solvent and surfactant, the surfactant can precipitate out. In various aspects, typically the concentrations of the salt, second solvent and surfactant are adjusted such that the continuous process medium is a homogeneous solution.

Any microparticle formation process utilizing a dispersed phase in a continuous process medium (a continuous phase system) can be utilized. Any process to form the emulsion can be used. Any process to remove the solvent can be used, such as, for example, a liquid-liquid extraction, solvent evaporation, or a combination thereof. The emulsion itself can be a single emulsion, such as an oil-in-water or a solid-in-oil-in-water, or a double emulsion, such as a water-oil-water emulsion. Double emulsions are typically formed by the agent not being fully soluble in the first solvent for the polymer.

An advantage of the present invention is that the presence of the salt in the continuous process medium reduces the solubility of the first and second solvents in the continuous process medium. Thus as the salt concentration increases, the first and second solvent solubility in the continuous process medium decreases. Even though the second solvent is saturated in the continuous process medium, when it is an organic solvent, less total organic solvent is required in the continuous process medium and in the overall system. This reduces the amount of extraction phase medium that is needed to remove any residual organic solvent. Additionally, lower quantities of organic solvent in the continuous phase medium results in lower total quantities of organic solvent in the overall processing system which provides for safer handling and more inexpensive waste disposal. Further, lower quantities of organic solvent in the continuous phase medium changes the sink conditions for extraction of the first solvent during subsequent processing steps used to remove solvent from the emulsion droplets, allowing for different processing conditions as compared to more standard emulsion systems. More generally, changes in continuous phase and extraction phase can affect separation and isolation of extracted microparticles, such as reducing required rinse water or reducing equipment requirements to transfer extraction suspension for collection.

Additionally, a cost savings is achieved by using salt while reducing the amount of second solvent, typically organic solvent, which is typically more costly than the salt. Additionally, the use of the salt in the continuous phase or the continuous process medium of the emulsion process has various advantages, including, improved properties of the final product, such as flowability, spherical shape and surface features of the particles, encapsulation efficiency, density, reduced initial burst and affect on longer-term release characteristics.

Further, the present methods and microparticles can provide for improved encapsulation efficiency and performance of the microparticle product. The addition of salts to the continuous phase (CP) medium can in various aspects affect the precipitation behavior of the polymer in the emulsion system. Solutions containing high salt concentrations can be used for precipitating polymers in a salting-out phenomenon. Thus, the polymers in the organic-phase of the microencapsulation emulsion can have their solubility properties affected by their exposure to the high-salt-containing CP medium and that, in-turn, affects the polymer precipitation properties of the system as compared to emulsion systems that do not contain high salt concentrations in the CP medium. The different polymer precipitation phenomena in the systems of the present invention, therefore, can be one cause for differences in bulk properties of the final product obtained as well as any differences obtained in encapsulation efficiency and performance of the microparticle product.

Extraction rate is directly dependent on the concentration gradient from the dispersed phase into the mixed continuous and extraction phase. Displacing solvent in the continuous phase with salt decreases the amount of solvent in mixed continuous and extraction phases. At low concentrations of salts, solubility of solvents is not affected. Because salt in the mixed continuous and extraction phases is extremely dilute, the concentration gradient for extraction of the microparticles is maximized. The presence of any solvent in mixed continuous and extraction phases decreases the concentration gradient, and associated extraction rate, for microparticle extraction. This greater rate of extraction precipitates polymer more rapidly having benefits of: (1) trapping agent within precipitated particles, (2) reducing surface porosity related to initial burst, and (3) creating smoother microspheres with decreased angle of repose (as defined in Example 3).

The method of the current invention, whereby both a salt and a solvent are utilized in the continuous process medium (i.e., continuous phase), can produce a microparticle with a static angle of repose (hereinafter "angle of repose" or "AOR"), as defined and as measured using a Hele-Shaw cell, smaller than the angle of repose for microparticles prepared with no salt in the continuous phase or no solvent in the continuous phase or no salt and no solvent in the continuous phase. That reduction in angle of repose can be as much as at least 5, 10, 15, 20, or 25 degrees lower for the salt and solvent process of the current invention as compared to the no salt, no solvent, or no salt/solvent cases. The resultant angle of repose of microparticles made by the process of the current invention can be as little as ≤35, ≤30, ≤25, ≤20, ≤18, or ≤17 degrees.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Figure 2:
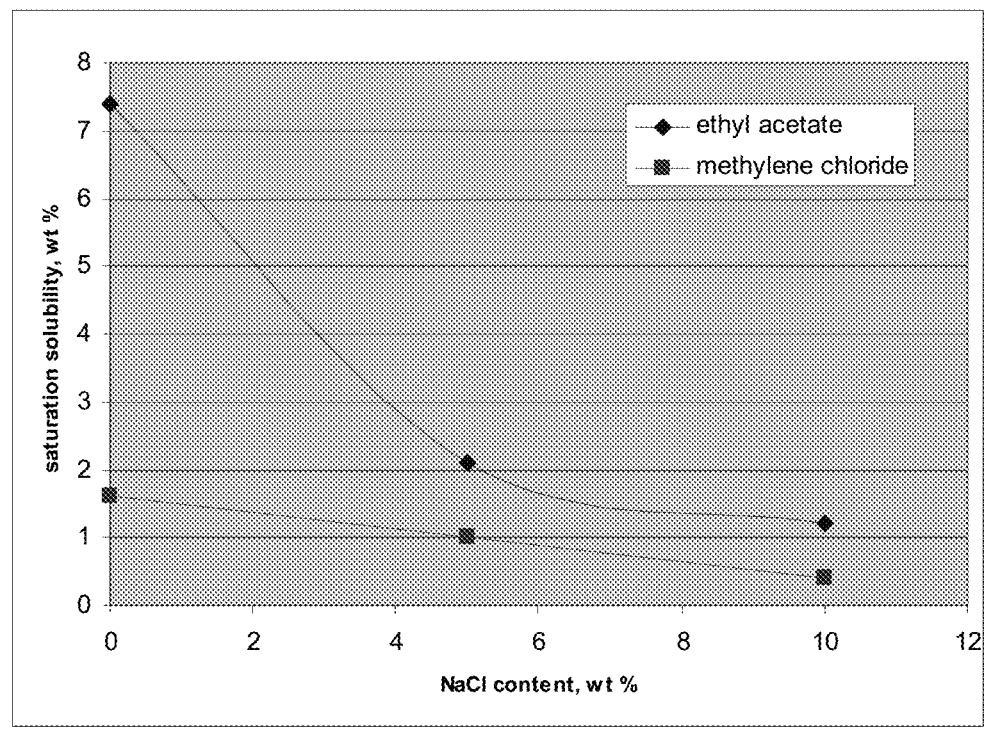
FIG. 2 is a graph showing the saturation solubility in weight percent for the organic solvents ethyl acetate and methylene chloride versus sodium chloride content in weight percent in a 1% PVA aqueous continuous phase solution.

An equilibrium/saturation study was performed to measure solvent solubilities in PVA solutions in increasing salt concentration levels. The saturation solubility in weight % of ethyl acetate and methylene chloride were individually tested with varying sodium chloride weight % in a 2% PVA aqueous solution. As can be seen from FIG. 1, as the sodium chloride content was increased, the saturation solubility of the two organic compounds decreased. At about 15 weight % sodium chloride contention, the PVA began to salt out of the solution. Similar trends are observed using a 1% PVA aqueous solution as is shown in FIG. 2.

Example 2

Microparticle formulations were made with a continuous phase (CP) system containing high salt concentration (2M)

both with and without added organic solvent in the CP system. Formulations were made by first emulsifying either 150 microliters or 300 microliters of an inner aqueous phase solution consisting of 0.1 wt % solution of poly(vinyl alcohol) (PVA) into 1.5 g polymer solution consisting of 25 wt % 50:50 poly(lactide-co-glycolide) (0.3 dL/g) (5050 PLG 3E) in ethyl acetate. The emulsification of the inner aqueous phase solution into the polymer solution was performed for 60 seconds with a Polytron PT10-35 mixer using a speed setting of 3. The resulting primary emulsion was used as the dispersed phase (DP) solution, which was emulsified into 50-g continuous phase (CP) solution consisting of 1 wt % PVA and 2M sodium chloride and, optionally, 3 wt % ethyl acetate. Emulsification of the DP into the CP was performed by slowly introducing the DP solution to the mixer head of an IKA Ultra-Turrax T-25 mixer (using a speed setting of 1) that was immersed in the CP solution. Emulsification was performed for 30 seconds at which time the resulting emulsion was poured into a beaker containing 140 g stirred extraction phase (EP) water. Extraction was carried out, while stirring, for 1 hour and then the resulting microparticle product was isolated from the suspension by collection over a 20-micron test sieve. The collected microparticle product was washed with approximately 2-L water. The product was then dried by lyophilization.

Figure 3A:
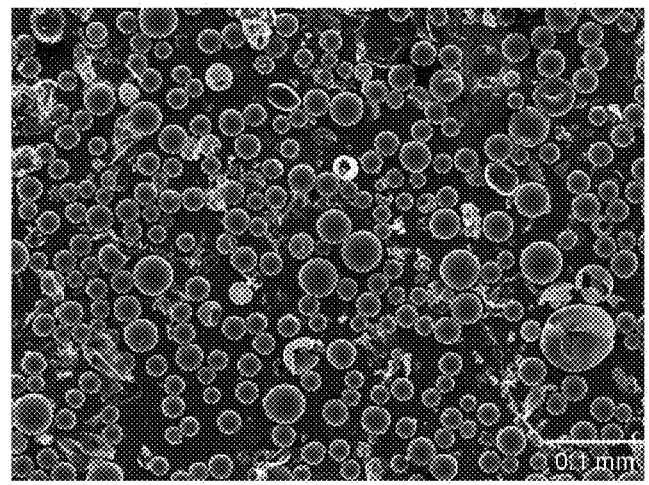
FIGS. 3A and 3B are scanning electron microscopy (SEM) images (250× magnification) of representative microparticle product produced from a double-emulsion process using a 150 microliter volume of internal aqueous phase and a continuous phase (CP) system comprising 2M sodium chloride (salt) and (a) no added organic solvent (lot 002161-0064); (b) saturated level of organic solvent (ethyl acetate) (lot 002161-063).
Figure 3B:
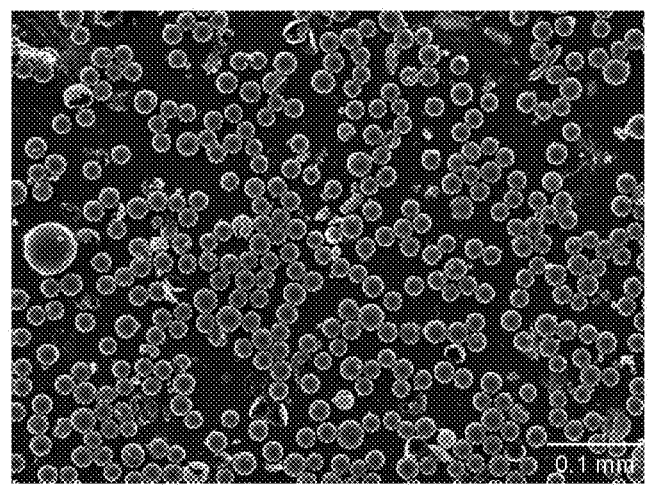
Figure 4A:
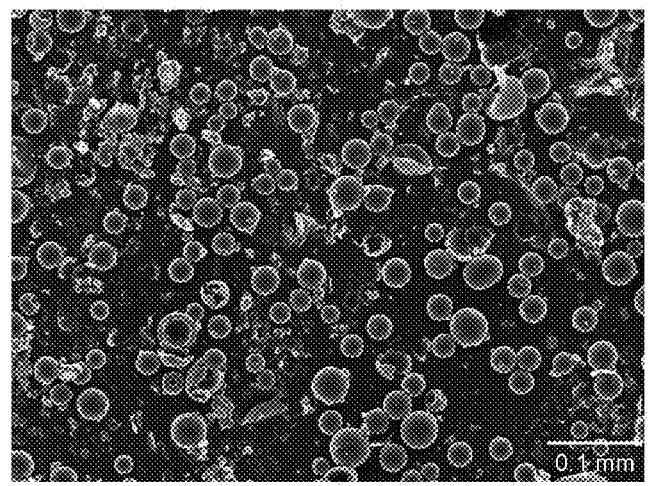
FIGS. 4A and 4B are scanning electron microscopy (SEM) images (250× magnification) of representative microparticle product produced from a double-emulsion process using a 300 microliter volume of internal aqueous phase and a continuous phase (CP) system comprising 2M sodium chloride (salt) and (a) no added organic solvent (lot 002161-0069); (b) saturated level of organic solvent (ethyl acetate) (lot 002161-068).
Figure 4B:
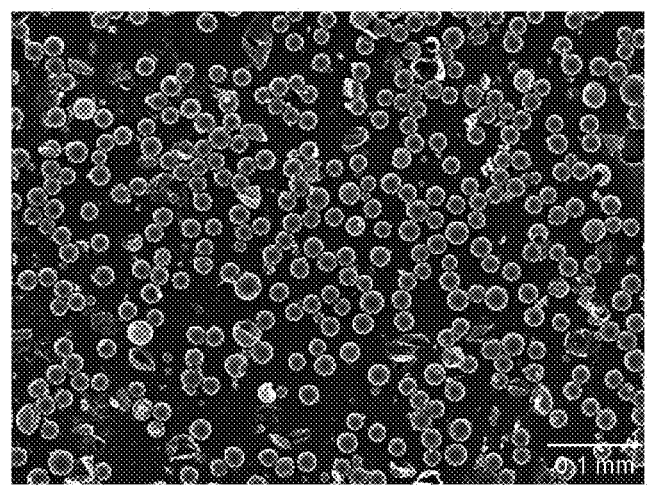

Scanning electron microscopy was used to take photomicrographs of samples prepared in this example. FIGS. 3A and 3B show images of representative microparticle product from formulations prepared using 150 microliters inner aqueous phase solution when using no additional organic solvent in the CP solution (FIG. 3a) and when using 3 wt % ethyl acetate in the CP solution (FIG. 3b). Similarly, FIGS. 4A and 4B show images of representative microparticle product from two similar formulations prepared using 300 microliters inner aqueous phase solution.

Comparison of SEM images in FIGS. 3A and 3B and 4A and 4B demonstrate that the addition of organic solvent to the salt-containing CP solution system can result in an improved microparticle product having a narrower particle size distribution, fewer irregular particles and/or less non-particle residue.

Example 3

Angle of repose is a technique used to characterize the flowability of solids such as powders. Improving the flowability of a powder is advantageous by providing better handling during powder filling and packaging operations, lower losses of material during transfer, and reduced aggregation. The U.S. Pharmacopeia (USP) General Chapter <1174>"Powder Flow" (reference: USP32/NF27) (2009) refers to four general methods that are commonly employed to characterize and compare powder flow characteristics, one of which is the Angle of Repose (AOR) method. The U.S. Pharmacopeia (USP) General Chapter <1174>"Powder Flow" USP32/NF27 (2009) is incorporated herein by this reference for its teachings of AOR measurements. The USP describes basic methods for assessing the AOR and identifies two important experimental variables that should be defined in any general method used to determine AOR: (1) funnel height should be specified as being either fixed or varied relative to the base during measurement; and (2) the base should be specified as being either of a fixed diameter or variable diameter during measurement. One technique commonly described in the literature for determining AOR is through the use of a Hele-Shaw cell. In this technique, the funnel height is kept at a fixed height during measurement (fixed relative to the base of the cell) and the base diameter is fixed during measurement.

Angle of repose measurements were performed on microparticle formulations using a Hele-Shaw cell. A Hele-Shaw cell was constructed of two plastic plates affixed parallel to one another with a gap of approximately 5 mm between the two plates. The plates were sealed on all sides. In one corner of the cell, a funnel was inserted into the cell to permit powder to be dropped down vertically along one edge of the cell. Samples were analyzed for angle of repose (AOR) as follows. The cell was firmly affixed to the bench top with the funnel positioned at the top of the cell pointing downwards. Approximately 2 grams of a microparticle formulation was added to the funnel and allowed to flow down the cell and accumulate at the bottom corner of the cell. Photographs were then taken of the resulting powder mass in order to capture the final height and width of the powder sample. AOR was then determined directly from photographs of individual determinations by directly measuring the angle at which the resulting powder sample rises up from the bottom (horizontal) edge of the Hele-Shaw cell (using a protractor). Triplicate experiments were performed on each microparticle formulation and results are reported as the mean and standard deviation (SD) of the triplicate determinations.

In this manner, smaller AOR's are associated with powder samples that are able to flow further in a horizontal direction away from spot to which the sample was dropped. As a result, smaller AOR's are directly associated with powder samples that have relatively better powder flow characteristics. Table 1 is taken directly from the Chapter <1174> in USP32/NF27 showing the relative trends between AOR and powder flow properties.

TABLE 1

Flow Properties and Corresponding Angle of Repose[1]

| Flow Property | Angle of Repose (degrees) |
| --- | --- |
| Excellent | 25-30 |
| Good | 31-35 |
| Fair (aid not needed) | 36-40 |
| Passable (may hang up) | 41-45 |
| Poor (must agitate, vibrate) | 46-55 |
| Very poor | 56-65 |
| Very, very poor | >66 |

[1]Reference: Chapter <1174> in USP32/NF27 (2009).

Three microparticle formulations were prepared using an emulsion-solvent extraction process. One lot was prepared with a continuous phase (CP) solution comprising high salt (2M sodium chloride), a second lot was prepared with a CP solution comprising a saturated level of organic solvent (7.5 wt % ethyl acetate), and a third lot was prepared with a CP solution comprising both high salt and a saturated level of organic solvent (2M sodium chloride and approximately 3% ethyl acetate). Otherwise, the CP solution in all cases further comprised 1 wt % PVA solution.

Microparticle formulations were prepared using a dispersed phase (DP) solution comprising 14.4 g 85:15 DLG (4.5E) poly(DL-lactide-co-glycolide) polymer (Brookwood Pharmaceuticals), 57.6 g ethyl acetate, and 14 mg coumarin-6. This DP solution was continuously emulsified into one of the continuous phase solutions described above using a Silverson L4RT mixer at a stir speed of approximately 1100 rpm. The resulting emulsion was immediately diluted with fresh deionized water as the extraction phase (EP) solvent.

Flow rates of the DP, CP, and EP were approximately 13 g/min, 125 g/min, and 1250 g/min, respectively. The resulting suspension was collected in a tank and stirred for one hour at which time the suspension was passed across 125-micron and 20-micron test sieves. The product collected on the 20-micron sieve was rinsed with 4-L deionized water and was then dried by lyophilization on a laboratory freeze dryer.

Results of AOR measurements are presented in Table 2. The sample prepared using a CP solution comprising both high salt and saturated level of organic solvent had a markedly lower AOR as compared to the samples prepared either with a CP solution comprising either the high salt alone or the saturated level of organic solvent. The 16.7° AOR for this sample reflects a sample having "excellent" flow properties (according to the criteria set forth in the USP) as compared with the other two samples which had AOR's of powders that are characterized by the USP as having "fair" to "poor" flow properties.

TABLE 2

Results of AOR determinations on microparticle formulations.

| CP solution composition | Angle of Repose (AOR), in degrees (mean (SD)) |
|---|---|
| 2M sodium chloride | 39.2 (2.0) |
| Saturated with ethyl acetate (7.5 wt %) | 46.0 (5.2) |
| 2M sodium chloride, saturated with ethyl acetate (3 wt %) | 16.7 (1.2) |

Example 4

Four microparticle formulations were made from a double-emulsion microencapsulation process in which the composition of the continuous phase (CP) solution was changed by either the presence or absence of 2M salt (sodium chloride) and the presence or absence of a saturating amount of organic solvent added to the CP solution. Formulations were made using dexamethasone sodium phosphate as a model hydrophilic drug and ethyl acetate as the organic processing solvent. Formulations were made by dissolving 1.25 grams of dexamethasone sodium phosphate into 2 grams deionized water. The resulting solution was used as an inner aqueous phase and was emulsified into 55 grams of polymer solution consisting of 20 wt % 75:25 poly(lactide-co-glycolide), 0.48 dL/g (7525 PLG 5E) in ethyl acetate. The emulsification of the inner aqueous phase solution into the polymer solution was performed in a continuous manner by pumping the aqueous and organic phases into an IKA ultra-Turrax T-25 mixer with inline mixer-head attachment (speed setting 6000 rpm). The two solutions were pumped into the mixer at a flow rate of 0.7 mL/min for the aqueous phase and 14.3 g/min for the organic phase. The resulting primary emulsion was used as the dispersed phase (DP) solution, which was emulsified into 725 grams continuous phase CP solution consisting of 2 wt % PVA and (optionally) 2M sodium chloride and (optionally) a saturating level of ethyl acetate (either 7.4 wt % ethyl acetate when no additional salt was used or 3.0 wt % ethyl acetate when 2M salt was present). Emulsification of the DP and CP was performed by introducing the DP and CP solutions at the inlet port of a Silverson mixer L4R-T mixer with laboratory in-line head assembly. The Silverson speed was set at 1700 rpm. The mix rates for the DP and CP solutions were 15 g/min and 125 g/min respectively. After passing the mixed DP and CP solutions through the mixer head, extraction water (EP) was added at a rate of 2.2 L/min. The combination of the three phases (DP, CP, and EP) was collected in a vessel which contents are stirred with a suitable mixer for 20 minutes to facilitate further solvent removal. The resulting microparticle product was isolated from the suspension by collection over 125 micron and 20 micron test sieve setup. The material collected on the 20 micron test sieve was used as the collected microparticle product. The material collected on the 125 micron sieve was discarded. The collected microparticle product was washed with approximately 2-L water. The product was allowed to air dry on the 20 micron test sieve under a laminar flow hood for 48 hours.

Samples of the dry microparticle product were then analyzed for drug content by HPLC. A known quantity of sample was dissolved in dimethylsulfoxide (DMSO), and water was added to the sample to precipitate the polymer. The resulting suspension was filtered to remove polymer and the remaining solution was analyzed by HPLC using a Phenomenex Luna C18 4.6×150 mm by Phenomenex (Torrance Calif.). Chromatography was performed on a 40-µl injection volume by an isocratic method using a mobile phase of 70% (by volume) 25 mM sodium phosphate pH 3 and 30% acetonitrile. Detection was performed by UV at 240 nm.

Results shown below demonstrate the encapsulation of the drug was improved by the use of a CP solution containing both a high salt content (2M sodium chloride) and a saturating level of organic solvent (3 wt % ethyl acetate).

Summary of Batches prepared:

| Batch | Added Salt in the CP | | Added Solvent in the CP | |
|---|---|---|---|---|
| | 2M | none | saturated | none |
| 1 | | ✓ | | ✓ |
| 2 | | ✓ | ✓ | |
| 3 | ✓ | | | ✓ |
| 4 | ✓ | | ✓ | |

TABLE 3

Dexamethasone sodium phosphate loading in model formulations prepared with and without 2M sodium chloride in the Continuous Phase (CP) processing solution.

| Batch | Drug content, wt % |
|---|---|
| 1 | 3.57 |
| 2 | 3.52 |
| 3 | 3.23 |
| 4 | 4.80 |

In summary, the batch prepared with both 2M salt and a saturating level of organic solvent added to the CP solution (batch 4) had a higher drug loading level (higher encapsulation efficiency) than those without either or both components.

While particular embodiments of the present disclosure have been illustrated and described, various other changes and modifications are enabled and can be made without departing from the spirit and scope of the disclosure. It is therefore intended to cover in the appended claims all such changes and modifications that are within the scope of this disclosure.

What is claimed is:

1. An encapsulation method for producing microparticles comprising (a) forming an emulsion or double emulsion comprising a dispersed phase comprising an agent, a polymer, and a first solvent for the polymer, in a continuous process medium, wherein the continuous process medium comprises at least one salt and at least one second solvent, wherein the second solvent reduces the solubility of the first solvent in the continuous process medium; and (b) extracting the first solvent from the dispersed phase to form the microparticles;

wherein the second solvent is in a saturating amount in the continuous process medium; wherein the first solvent comprises ethyl acetate or methylene chloride;

wherein the second solvent comprises ethyl acetate or methylene chloride; wherein the first and second solvents are the same solvent; and wherein the microparticles having an angle of repose of ≤35, as measured using a Hele-Shaw cell.

2. The method of claim 1, wherein the salt comprises sodium chloride.

3. The method of claim 1, wherein the salt comprises potassium chloride.

4. The method of claim 1, wherein the salt is in a concentration in the continuous process medium of from 0.1 to 20 wt %.

5. The method of claim 1, wherein the second solvent comprises two or more solvents.

6. The method of claim 1, wherein the continuous process medium further comprises water.

7. The method of claim 1, wherein the continuous process medium further comprises substantially water.

8. The method of claim 1, wherein the continuous process medium further comprises a surfactant.

9. The method of claim 8, wherein the surfactant comprises PVA.

10. The method of claim 1, wherein the dispersed phase and continuous process medium forms an emulsion.

11. The method of claim 1, wherein the dispersed phase and continuous process medium forms a double emulsion.

12. The method of claim 1, wherein the temperature of the continuous process medium is adjusted from ambient temperature to decrease the solubility of the first solvent in the continuous process medium.

13. The method of claim 1, wherein the temperature of the continuous process medium is adjusted from ambient temperature to increase the solubility of the first solvent in the continuous process medium.

14. The method of claim 1, wherein the angle of repose of the resultant microparticles is at least 10 degrees less than the angle of repose of the resultant microparticles made without a salt and/or solvent in the continuous process medium.

15. The method of claim 1, wherein the angle of repose of the resultant microparticles is at least 15 degrees less than the angle of repose of the resultant microparticles made without a salt and/or solvent in the continuous process medium.

16. The method of claim 1, wherein the angle of repose of the resultant microparticles is at least 20 degrees less than the angle of repose of the resultant microparticles made without a salt and/or solvent in the continuous process medium.

17. An emulsion comprising a dispersed phase comprising an agent, a polymer, and a first solvent for the polymer and a continuous phase comprising a polymer non-solvent, a second solvent, wherein the second solvent reduces the solubility of the first solvent in the polymer non-solvent, and a salt that reduces the solubility of the first solvent in the polymer non-solvent.

* * * * *